United States Patent [19]

Holzermer et al.

[11] 3,976,887
[45] Aug. 24, 1976

[54] X-RAY EXAMINATION APPARATUS

[75] Inventors: Günter Holzermer; Günter Schmitt, both of Erlangen, Germany

[73] Assignee: Siemens Aktiengesellschaft, Erlangen, Germany

[22] Filed: Mar. 27, 1975

[21] Appl. No.: 562,455

[30] Foreign Application Priority Data

Apr. 11, 1974 Germany............................ 2417891

[52] U.S. Cl.................................. 250/468; 250/471
[51] Int. Cl.². ......................................... G03B 41/16
[58] Field of Search ........... 250/468, 471, 511, 512, 250/513, 444

[56] References Cited
UNITED STATES PATENTS 3,829,698   8/1974   Goetz.................................. 250/468

Primary Examiner—Craig E. Church
Attorney, Agent, or Firm—Haseltine, Lake & Waters

[57] ABSTRACT

An X-ray examination apparatus, including an adjustable optical X-ray diaphragm or focusing means; and an examination table having a cassette drawer carriage displaceable along the examination table located directly below the patient support platform of the examination table, and a cassette drawer which is insertable into the cassette drawer carriage having two pairs of clamping members each with two mutually oppositely movably adjustable clamping jaws for the retention of the X-ray film cassettes inserted into the cassette drawer. In an X-ray examination apparatus of the above-mentioned type, each clamping jaw pair is itself displaceable within the cassette drawer in the two adjusting directions for the associated clamping jaws, at the clamping of an X-ray film cassette in the cassette drawer, pursuant to the selected film division. Thereby, it becomes possible that also larger film formats can be rationally employed, and to be able to combine a plurality of X-ray exposures or photographs of a patient on a single film plate. The manipulation of the cassette drawer is rendered particularly easy when a motorized adjustment of the clamping jaw pairs is provided for in dependence upon the selected film division or partitioning program, and the particular division sections. In this instance, a plurality of X-ray exposures may be initiated within time intervals of a few seconds.

6 Claims, 2 Drawing Figures

X-RAY EXAMINATION APPARATUS

FIELD OF THE INVENTION

The present invention relates to an X-ray examination apparatus, including an adjustable optical X-ray diaphragm or focusing means, and an examination table having a cassette drawer carriage displaceable along the examination table located directly below the patient support platform of the examination table, and a cassette drawer which is insertable into the cassette drawer carriage having two pairs of clamping members each with two mutually oppositely movably adjustable clamping jaws for the retention of the X-ray film cassettes inserted into the cassette drawer.

DISCUSSION OF THE PRIOR ART

A control installation for confining the utilizable X-ray beam of an X-ray tube is known wherein, upon the insertion of an X-ray film cassette into the cassette retainer of an X-ray examination apparatus, two continually variable measurement value transducers in the cassette retainer may be adjusted through displacement of the clamping jaws. Through the intermediary of the measurement value transducers, the focusing means which are located on the X-ray tube are set according to the dimensions of the inserted X-ray film cassette. Notwithstanding this automization, the operation with an X-ray film cassette which is inserted into a cassette drawer remains relatively difficult since, for each individual X-ray exposure, a new X-ray film cassette must be inserted. Moreover, it has so been found as a drawback that the film plate or sheet which is located within the X-ray film cassette is only incompletely utilized, and in particular when, during the examination of extremities, operation must be effected with long, narrow focuses.

SUMMARY OF THE INVENTION

Accordingly, it is an object of the present invention to widen the range of applicability of the cassette drawers and, namely, to seek ways which facilitates an improved film utilization in cassette drawers. In an X-ray examination apparatus of the above-mentioned type, in an inventive manner, each clamping jaw pair is itself displaceable within the cassette drawer in the two adjusting directions for the associated clamping jaws, at the clamping of an X-ray film cassette in the cassette drawer, pursuant to the selected film division. Thereby, it becomes possible that also larger film formats can be rationally employed, and to be able to combine a plurality of X-ray exposures or photographs of a patient on a single film plate. The utilization of the film material is thus, above all, considerably improved in such instances in which narrow focuses are required during the examination of extremities. Finally, in this manner, it is also possible to complete a plurality of X-ray exposures in immediate sequence without the need for cassette changing.

The manipulation of the cassette drawer is rendered particularly easy when a motorized adjustment of the clamping jaw pairs is provided for in dependence upon the selected film division or partitioning program, and the particular division sections. In this instance, a plurality of X-ray exposures may be initiated within time intervals of a few seconds. This particularly is of great advantage in the field of angiography.

In a practical embodiment of the invention, the drive means for effecting the adjustment of the clamping jaw pairs may be located on a small plate which is applied to the lower side of the cassette drawer facing away from the X-ray source, and connectable to the two carriers of the clamping jaw pairs by means of a follower pin or tang projecting through slots formed in the floor of the cassette drawer. Hereby it also becomes possible for a physician having a smaller practice to initially acquire the cassette drawer without the small plate having the motorized drive and, in accordance with need, at a later timepoint through an additional purchase to provide his X-ray examination apparatus at the lower side of the cassette drawer with the insertable plate having the motorized drive.

In a particularly advantageous further embodiment of the invention, there may be provided, at the crossing point of two clamping jaws, a rider concurrently sliding on the two clamping jaws forming a carrier for markings or indicia which are reproducible by the X-rays. Such a carrier affords the advantage that the markings which are fastened onto the rider are always photographed in the same corner of the X-ray film cassette, independently of the cassette format and of the selected film partitioning.

The operation of the cassette drawer may be rendered much more confortable when, in an embodiment of the invention, respectively one of the clamping jaws of each of the clamping jaw pairs has associated therewith a sideways projecting follower lug or tang relative to the inserting direction of the cassette drawer, for the automatic opening of the clamping jaws during cassette exchange, and a contact being provided in the cassette drawer carriage adapted to be brought into engagement with the follower lug or tang during the withdrawal of the cassette drawer. Through this construction, the clamping jaws spread during the withdrawal of the cassette drawer, so that the withdrawal of the exposured X-ray film cassette and the insertion of a new X-ray film cassette may be carried out in the simplest possible manner.

BRIEF DESCRIPTION OF THE DRAWINGS

Further details of the invention may now be ascertained from the following description of an exemplary embodiment thereof, taken in conjunction with the accompanying drawings; in which.

DETAILED DESCRIPTION

Figure 1:
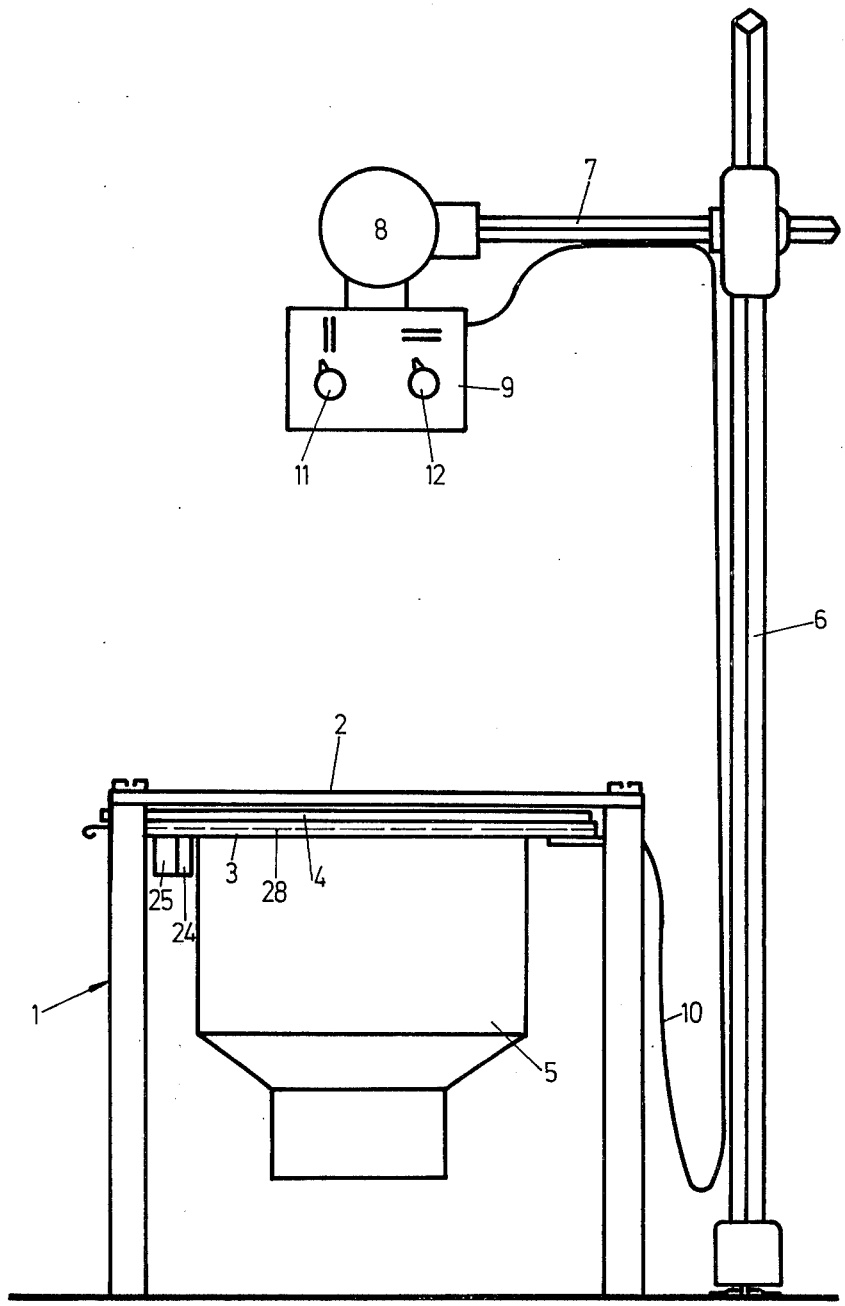
FIG. 1 shows a side elevational view of an X-ray examination apparatus incorporating a cassette drawer pursuant to the invention.

Referring now in detail to the drawings, FIG. 1 illustrates, in a side elevational view, an X-ray examination apparatus having an X-ray examination table 1. Shown below the patient support platform 2 is cassette drawer carriage 3 which is slidable along the longitudinal direction of the table, and having a cassette drawer 4 inserted therein. Additionally, below the examination table 1 there is also provided a picture amplifier-video installation 5 which is similarly slidably displaceable in the longitudinal direction of the table. Adjacent the examination table there may be recognized a support column 6 which is adapted to be conveyed about the floor and which, on a horizontally-extending arm 7, supports above the examination table an X-ray tube 8 and an X-ray diaphragm or focusing arrangement 9. The X-ray focusing diaphragm 9 is provided with a suitable electrical follower or servo control (not shown), and is connected to the examination table through an electrical cable 10.

Figure 2:
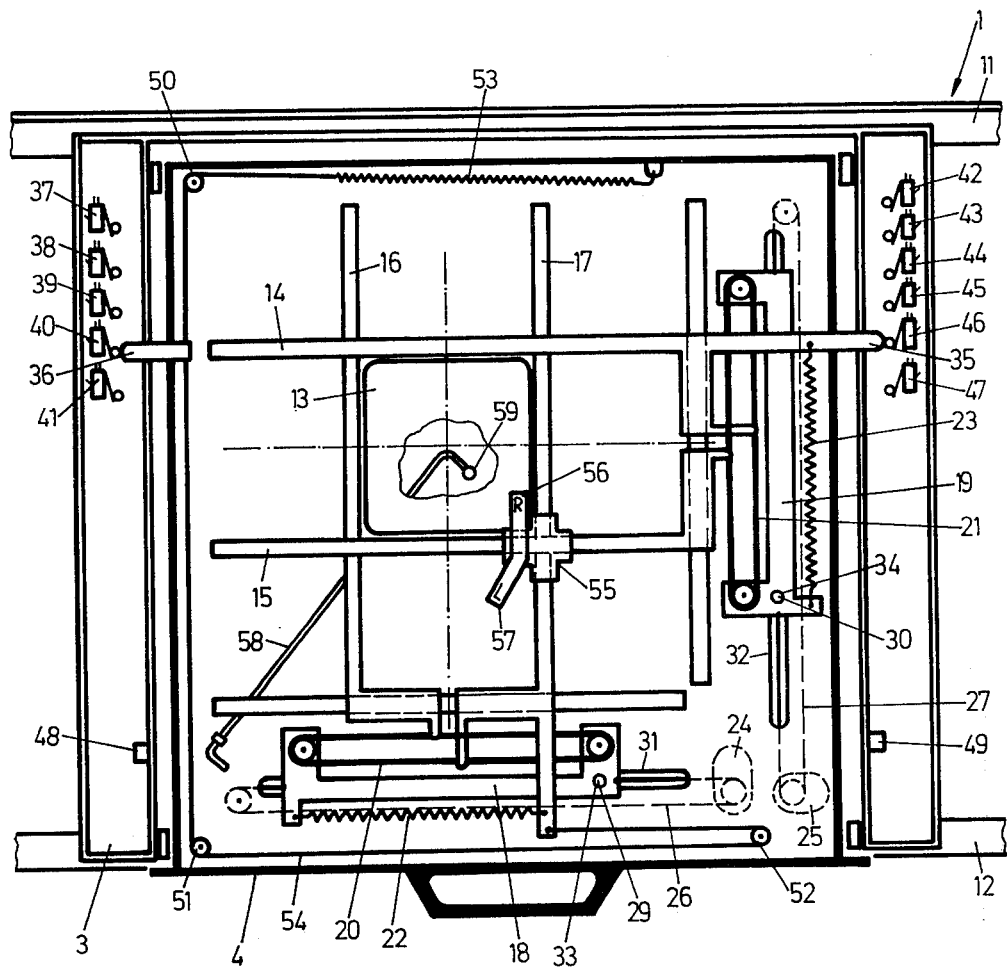
FIG. 2 shows a top plan view of the cassette drawer carriage illustrated with the cassette drawer inserted therein.

As shown in FIG. 2 of the drawings, which discloses the top plan view of the examination table 1 with the patient support platform having been removed therefrom for purposes of clarity, there may be seen the cassette drawer carriage 3 which is slidable along the longitudinal spans 11, 12 of the examination table, and a cassette drawer 4 inserted into the cassette drawer carriage transversely of the sliding direction the cassette drawer carriage. Shown clamped in the cassette drawer is an X-ray film cassette 13 between the clamping jaws 14, 15, 16 and 17. The clamping jaws are each carried in a paired manner on a carrier 18, 19, and are each mutually oppositely adjustably supported on the carriers by means of, respectively, traction cord 20, 21. The clamping jaws of each of the clamping jaw pairs are pressed against the inserted X-ray film cassette 13 through the action of a tension spring 22, 23. The two carriers 18, 19 for the two clamping jaw pairs are, in turn, supported within the cassette drawer so as to be displaceable in the adjusting direction of the associated clamping jaws through the intermediary of a toothed-belt pull 26, 27 each driven by, respectively, a motor 24, 25. The two motors with the toothed-belt pulls are, in turn, mounted on a small plate 28 which is fastened directly below the cassette drawer (FIG. 1). Clamped onto each of the two toothed-belt pulls 26, 27 is a follower plug 29, 30 which project through slots 31, 32 in the floor of the cassette drawer into bore 33, 34 formed in carriers 18, 19 for the particular clamping jaw pair. Respectively one of the clamping jaws 14, 17 of each of the clamping jaw pairs has a follower tang 35, 36 associated therewith, which projects sidewise from the cassette drawer relative to the inserting direction of the cassette drawer 4 into the cassette drawer carriage 3. These follower tangs 35, 36, for an inserted cassette drawer, find themselves in engagement with contact banks 37 through 47 located on the sides of the cassette drawer in the cassette drawer carriage for effecting control over the focusing diaphragm 9, and for the control of the motors 24, 25 of the toothed-belt pulls. Upon the withdrawal of the cassette drawer 4 from the cassette drawer carriage 3, they then lie against a contact 48, 49, each fixedly located in the cassette drawer carriage, so that the clamping jaws 14, 15, 16, 17 are pulled apart during the further withdrawal of the cassette drawer from the cassette drawer carriage. The follower tang 35 of the clamping jaw 14 which is displaceable in the direction of insertion, is formed as an extension of this clamping jaw. For the clamping jaw 17 which is adjustable transverse to the inserting direction of the cassette drawer 4, the associated follower tang 36 is fastened to a traction cord 54 which is conveyed with the cassette drawer by means of three sheaves 50, 51, 52, and which is tensioned by a spring 53. At the intersecting point of the two clamping jaws 15, 17, shown in the lower right-hand portion in FIG. 2, a rider 55 is mounted having guides concurrently sliding on the two clamping jaws. On the rider there are pivotally mounted markings 56, 57 which may be copied or photographed by the X-rays. Conveyed along the floor of the cassette drawer 4 is a plastic rod 58 so as to extend along a diagonal into the center of the cassette drawer 4, and is there bent through an angle of 90° into kind of a finger. Fastened to the end of the bent-over finger 90° is a lead sphere 59 which, upon pivoting of the rod 58 about its longitudinal axis, may be swung up into the plane of the inserted film plate which is located in an x-ray film cassette.

Upon the withdrawal of the cassette drawer 4 from the cassette drawer carriage 3, both of the follower tangs 35, 36 lie against the two contacts 48, 49 which are fastened in the cassette drawer carriage. Thereby, upon the further withdrawal of the cassette drawer from the cassette drawer carriage, the tangs pull the clamping jaw pairs 14, 15, 16, 17 apart against the force of springs 22, 23. The inserted x-ray film cassette 13 is thereby released. The cassette may then be manually removed without difficulty from the cassette drawer, and replaced with another X-ray film cassette having a fresh unexposed X-ray film plate therein. Upon the reinsertion of the cassette drawer 4, the follower tangs 35, 36 release from the contacts 48, 49, and the clamping jaws are moved toward each other through the action of the springs 22, 23 so that the X-ray film cassette 13 is centered in the middle of the cassette drawer 4. Concurrently, the rider 55 slides on the two mutually intersecting clamping jaws 15, 16 in the right-hand lower corner of the inserted X-ray film cassette. The markings 56 provided on the rider, in the embodiment of FIG. 2 representing an "R" is then imaged or photographed during the subsequent X-ray exposure through the X-rays on the right-hand lower corner of the film plate which is located in the X-ray film cassette. At a fully inserted cassette drawer 4, the contact banks 37 through 47 located in the cassette drawer carriage 3 are actuated by the follower tangs 35, 36 in accordance with the format of the inserted X-ray film cassette 13. By means of these contacts, the X-ray focusing arrangement or diaphragm 9 may then be automatically adjusted to the cassette format through a suitable follower or servo control (not shown). If a narrower focusing of the X-ray cone is selected, which permits for only a partial exposure of the inserted X-ray film plate, then the two carriers 18, 19 for the clamping jaw pairs 14, 15, 16, 17 are so far displaced by means of the motor-driven toothed-belt pulls 26, 27, as may be required for the selected film separation and the particular part section. After reaching the particular new exposure position, the motor-driven toothed-belt pulls are again placed at-rest by means of the contact banks 37 through 47 which are actuated by the follower lugs or tangs 35, 36. Due to this constructive embodiment of the cassette drawer 4, there may also be undertaken film divisions in the cassette drawers. Thereby, during the examination of extremities, it is possible to achieve for the frequently long and narrow focusing of the X-ray exposure an essentially better degree of film utilization.

In the employment of the cassette drawer 4 on x-ray examination apparatus, which facilitate the division of tomographic X-ray exposures, the correct setting of the planar elevation, for an uninserted X-ray film cassette, may be controlled by rotation of the rod 58 about its longitudinal axis. Thereby, the end of the finger with the lead sphere 59 is swung up into the film plane. At a correctly set planar elevation, the imaged layer does not displace during tomographic exposure cycle, meaning at the pivoting of the X-ray tube, in contrast with the upwardly swung lead sphere. Thereby, during transilluminating or tomographic exposure operation, when the picture amplifier-video installation is slid below the cassette drawer as measured in the direction of the X-rays, it may be easily observed and controlled.

While there has been shown what is considered to be the preferred embodiment of the invention, it will be obvious that modifications may be made which come within the scope of the disclosure of the specification.

What is claimed is:

1. In an X-ray examination apparatus having an adjustable X-ray focusing diaphragm; an examination table with a patient's support platform; an X-ray cassette drawer carriage slidable directly below said patient's support platform in the longitudinal direction of said examination table; and a cassette drawer insertable into said cassette drawer carriage including two pairs of clamping jaws, each said pair having two mutually oppositely adjustable clamping jaws for the retention of X-ray film cassettes inserted into said cassette drawer, the improvement comprising: means for moving the pairs of clamping jaws while clampingly engaging said cassettes independently of the sliding of said carriage below said patient's platform; and means for slidingly adjusting the pairs of clamping jaws in two directions of movement of the clamping jaws associated therewith at the clamping thereof of an X-ray film cassette pursuant to a selected film division within said cassette drawer.

2. An X-ray examination apparatus as claimed in claim 1, said last-mentioned means comprising motor-driven means for setting said pairs of clamping jaws dependent upon the selected film division program and a particular part section thereof.

3. An X-ray examination apparatus as claimed in claim 2, comprising a plate fastened to the floor of said cassette drawer on the surface facing away from a source of said X-rays, said motor-driven means for setting said clamping jaw pairs being mounted on said plate; carrier means for said pairs of clamping jaws; and follower lug means connected to said plate projecting through slots formed in the floor of said cassette drawer for engaging said carrier means.

4. An X-ray examination apparatus as claimed in claim 1, comprising rider means being concurrently slidingly supported on the crossing point of two of said clamping jaws, said rider means being a carrier for markings adapted to be imaged by X-rays.

5. An X-ray examination apparatus as claimed in claim 1, comprising a follower lug projecting sideways of the inserting direction of said cassette drawer being located on respectively one clamping jaw of each pair of clamping jaws; and contact means in said cassette drawer carriage adapted to be engaged by an associated follower lug during withdrawal of the cassette drawer for effecting the automatic opening of said clamping jaws for changing cassettes.

6. An X-ray examination apparatus as claimed in claim 1, comprising a rod being pivotably mounted on the floor of said cassette drawer; an upwardly swingable finger having an upwardly swingable lead sphere being on one end of said rod for controlling the setting of a planar layer during tomographic operation of said apparatus for an uninserted x-ray film cassette.

* * * * *